United States Patent [19]

Bundy

[11] 4,191,837

[45] Mar. 4, 1980

[54] TRANS-2,3,13,14-TETRADEHYDRO-9-DEOXY-9-METHYLENE-ω-ARYL-PGF COMPOUNDS

[75] Inventor: Gordon L. Bundy, Portage, Mich.

[73] Assignee: The Upjohn Company, Kalamazoo, Mich.

[21] Appl. No.: 933,000

[22] Filed: Aug. 11, 1978

Related U.S. Application Data

[62] Division of Ser. No. 893,771, Apr. 5, 1978, Pat. No. 4,165,436.

[51] Int. Cl.[2] .......................................... C07C 177/00

[52] U.S. Cl. ...................................... 560/55; 562/465; 260/398; 260/408; 260/410; 260/410.5; 260/410.9 R; 260/413

[58] Field of Search .......................... 560/55; 562/465; 260/398, 408, 410, 410.5, 410.9, 413

*Primary Examiner*—Paul J. Killos
*Attorney, Agent, or Firm*—Robert A. Armitage

[57] ABSTRACT

The present specification relates to novel 9-deoxy-9-methylene-trans-2,3-didehydro-PGF compounds with improved pharmacological properties. While these compounds are useful in inducing a wide variety of prostaglandin-like pharmacological effects, they are specifically useful as regulators of procreation and fertility.

14 Claims, No Drawings

TRANS-2,3,13,14-TETRADEHYDRO-9-DEOXY-9-METHYLENE-ω-ARYL-PGF COMPOUNDS

The present application is a divisional application of Ser. No. 893,771, filed Apr. 5, 1978, now U.S. Pat. 4,165,436, issued Aug. 21, 1979.

The present invention relates to prostaglandin analogs, for which the essential material constituting disclosure therefor is incorporated by reference here from U.S. Pat. No. 4,165,436.

I claim:

1. A prostaglandin analog of the formula

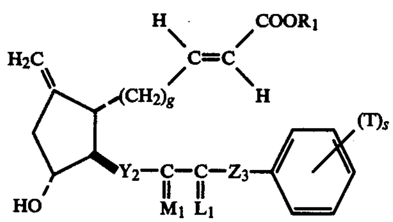

wherein $Y_2$ is —C≡C—;
wherein $M_1$ is

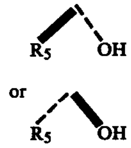

wherein $R_5$ is hydrogen or methyl;
wherein $L_1$ is

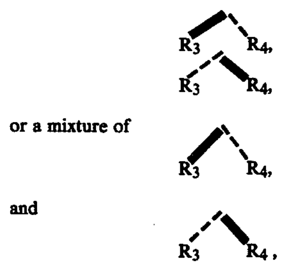

wherein $R_3$ and $R_4$ are hydrogen, methyl, or fluoro, being the same or different, with the proviso that one of $R_3$ and $R_4$ is fluoro only when the other is hydrogen or fluoro;

wherein g is 4, 5, or 6, wherein $Z_3$ is oxa or —$(CH_2)_h$—, wherein h is zero, one, two, or three; wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $Z_3$ is oxa only when $R_3$ and $R_4$ are hydrogen or methyl, being the same or different; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two or three chloro or alkyl of one to 3 carbon atoms, inclusive, or a pharmacologically acceptable cation.

2. A prostaglandin analog according to claim 1, wherein $Z_3$ is

—$(CH_2)_h$—.

3. 9-Deoxy-9-methylene-17-phenyl-18,19,20-trinor-trans-2,3,13,14-tetradehydro-$PGF_1$, a prostaglandin analog according to claim 2.

4. A prostaglandin analog according to claim 1, wherein $Z_3$ is oxa.

5. A prostaglandin analog according to claim 1, wherein g is 4.

6. A prostaglandin analog according to claim 5, wherein at least one of $R_3$ and $R_4$ is methyl.

7. 9-Deoxy-9-methylene-16,16-dimethyl-trans-2,3,13,14-tetradehydro-16-phenoxy-17,18,19,20-tetranor-$PGF_1$, a prostaglandin analog according to claim 6.

8. 9-Deoxy-9-methylene-16,16-dimethyl-trans-2,3,13,14-tetradehydro-16-phenoxy-17,18,19,20-tetranor-$PGF_1$, methyl ester, a prostaglandin analog according to claim 6.

9. A prostaglandin analog according to claim 5, wherein $R_3$ and $R_4$ are both hydrogen.

10. A prostaglandin analog according to claim 9, wherein $R_5$ is methyl.

11. 9-Deoxy-9-methylene-15-methyl-trans-2,3,13,14-tetradehydro-16-phenoxy-17,18,19,20-tetranor-$PGF_1$, a prostaglandin analog according to claim 10.

12. A prostaglandin analog according to claim 11, wherein $R_5$ is hydrogen.

13. 9-Deoxy-9-methylene-trans-2,3,13,14-tetradehydro-16-phenoxy-17,18,19,20-tetranor-$PGF_1$, methyl ester, a prostaglandin analog according to claim 12.

14. 9-Deoxy-9-methylene-trans-2,3,13,14-tetradehydro-16-phenoxy 17,18,19,20-tetranor-$PGF_1$, a prostaglandin analog according to claim 12.

* * * * *

UNITED STATES PATENT OFFICE
CERTIFICATE OF CORRECTION

Patent No. 4,191,837 Dated 4 March 1980

Inventor(s) Gordon L. Bundy

It is certified that error appears in the above-identified patent and that said Letters Patent are hereby corrected as shown below:

Column 2, line 45, "according to claim 11," should read -- according to claim 9 --.

Signed and Sealed this

*Second* Day of *September 1980*

[SEAL]

*Attest:*

SIDNEY A. DIAMOND

*Attesting Officer*

*Commissioner of Patents and Trademarks*